United States Patent
Wu et al.

(10) Patent No.: US 11,781,118 B2
(45) Date of Patent: Oct. 10, 2023

(54) PREPARATION OF L-AMINO ACID DEAMINASE MUTANT AND APPLICATION THEREOF

(71) Applicant: Jiangnan University, Wuxi (CN)

(72) Inventors: Jing Wu, Wuxi (CN); Shanshan Pei, Wuxi (CN); Jia Liu, Wuxi (CN); Wei Song, Wuxi (CN); Xiulai Chen, Wuxi (CN); Qiuling Luo, Wuxi (CN)

(73) Assignee: Jiangnan University, Wuxi (CN)

( * ) Notice: Subject to any disclaimer, the term of this patent is extended or adjusted under 35 U.S.C. 154(b) by 208 days.

(21) Appl. No.: 17/351,318

(22) Filed: Jun. 18, 2021

(65) Prior Publication Data

US 2021/0309974 A1 Oct. 7, 2021

Related U.S. Application Data

(63) Continuation of application No. PCT/CN2020/130330, filed on Nov. 20, 2020.

(30) Foreign Application Priority Data

Mar. 17, 2020 (CN) .......................... 202010185968.1

(51) Int. Cl.
*C12N 9/06* (2006.01)
*C12P 7/40* (2006.01)

(52) U.S. Cl.
CPC .............. *C12N 9/0022* (2013.01); *C12P 7/40* (2013.01); *C12Y 104/03002* (2013.01)

(58) Field of Classification Search
None
See application file for complete search history.

(56) References Cited

FOREIGN PATENT DOCUMENTS

| CN | 108841844 A | 11/2018 |
| CN | 109321541 A | 2/2019 |
| CN | 111269900 A | 6/2020 |
| KR | 20090088630 A | 8/2009 |

OTHER PUBLICATIONS

Chica et al. Curr Opin Biotechnol. Aug. 2005;16(4):378-84 (Year: 2006).*
Singh et al. Curr Protein Pept Sci. 2017, 18, 1-11 (Year: 2017).*
PCT/CN2020/130330. Written Opinion of the International Searching Authority. Feb. 23, 2021 (Year: 2021).*
Accession BFW78638. Feb. 7, 2019 (Year: 2019).*
Nshimiyimana et al. , Bioengineered, 10:1, 43-51,Published online: Mar. 27, 2019 (Year: 2019).*
Li et al. RSC Adv., 2017, 7, 6615-6621 (Year: 2017).*
Bornscheuer et al. Curr Protoc Protein Sci. Nov. 2011;Chapter 26:Unit26.7. (Year: 2011).*
Yoshikuni et al. Curr Opin Chem Biol. Apr. 2007;11(2):233-9. (Year: 2007).*
Wang, Yue et. al. Molecular modification of L-amino acid deaminase and optimizaiton of a-ketoglutaric acid production by whole cell biocatalysis, China Biotechnology, vol. 39, No. 3,2019.
Quan Zhang, et. al. Recent advances in enzymatic production of alpha-keto acids, Chinese J. Biotech. Jul. 25, 2019, 35(7) 1193-1205.

* cited by examiner

*Primary Examiner* — Christian L Fronda
(74) *Attorney, Agent, or Firm* — IPRO, PLLC; Na Xu

(57) ABSTRACT

The disclosure discloses preparation of an L-amino acid deaminase mutant and application thereof, belonging to the technical field of gene engineering. Through pmirLAAD protein modification, analysis of a flexible loop structure around a binding site of the pmirLAAD product, and design of the best mutant, the modification method of the disclosure overcomes the defect that the catalytic efficiency of the previous wild-type enzyme is reduced due to product inhibition, and is tested by experiments. Compared with the control, the catalytic efficiency (1.61 mM$^{-1}$·min$^{-1}$) and the product inhibition constant (5.4 mM) of the finally obtained best mutant pmirLAAD$^{M4}$ are respectively increased by 5.2 times and 5.7 times. The yield of α-ketoisovaleric acid can reach 96.5 g/L, and the transformation rate is greater than 97%. By adopting the method of the disclosure, the cost can be greatly reduced, and the industrialization process of production of α-ketoisovaleric acid by an enzymatic transformation method is accelerated.

8 Claims, 1 Drawing Sheet

Specification includes a Sequence Listing.

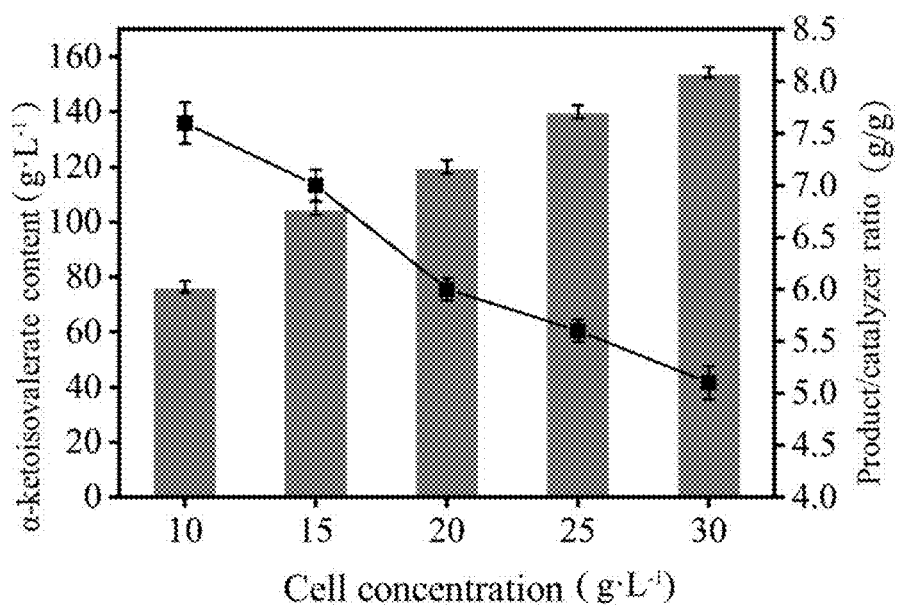

PREPARATION OF L-AMINO ACID DEAMINASE MUTANT AND APPLICATION THEREOF

TECHNICAL FIELD

The disclosure relates to preparation of an L-amino acid deaminase mutant and application thereof, belonging to the technical field of gene engineering.

BACKGROUND

L-amino acid deaminase (LAAD) is a flavin oxidase that can catalyze production of α-keto acids from L-amino acids. Researchers have done a lot of research on the spatial structure, substrate specificity and catalytic ability of L-amino acid deaminase to unnatural substrates. In recent years, the application of L-amino acid deaminase in the production of α-keto acids by biotransformation has gradually attracted the attention of the researchers.

α-keto acid is an important intermediate and is mainly used in the fields of food, medicines, cosmetics and the like, which makes enzymatic transformation of α-keto acids be widely used in industrial production. L-amino acid deaminase is a flavin protease. The oxidative deamination reaction of L-amino acids can include two steps: first, hydrogen on the amino acid Cα is transferred to FAD, and the amino acid becomes an imino acid, which is unstable and is decomposed into α-keto acid and water. Then, $FADH_2$ is oxidized by oxygen molecules and becomes reduced FAD. L-amino acid deaminase has wide substrate spectrum and high catalytic efficiency, which makes it possible to produce α-ketoisovaleric acid by transforming L-valine with heterologously expressed amino acid deaminase.

SUMMARY

The disclosure provides an LAAD mutant capable of being efficiently prepared and a modification method thereof, and preparation of α-ketoisovaleric acid by catalyzing L-valine with the mutant protein. The strain constructed by the disclosure has high catalytic activity in the preparation of α-ketoisovaleric acid, and greatly enhances the production efficiency of industrial production.

The disclosure provides an L-amino acid deaminase mutant. The mutant uses L-amino acid deaminase (pmirLAAD) derived from *Proteus mirabilis* as a parent, and the amino acid sequence of the parent L-amino acid deaminase is shown in SEQ ID NO: 1.

In one implementation, the nucleotide sequence encoding the L-amino acid deaminase parent is shown in SEQ ID NO: 2.

In one implementation, relative to the pmirLAAD parent, the amino acid at position 98 of the mutant is mutated, that is, serine is mutated into alanine to obtain a mutant S98A.

In one implementation, relative to the pmirLAAD parent, the amino acid at position 105 of the mutant is mutated, that is, threonine is mutated into alanine to obtain a mutant T105A.

In one implementation, relative to the pmirLAAD parent, the amino acid at position 106 of the mutant is mutated, that is, serine is mutated into alanine to obtain a mutant S106A.

In one implementation, relative to the pmirLAAD parent, the amino acid at position 341 of the mutant is mutated, that is, leucine is mutated into alanine to obtain a mutant L341A.

In one implementation, relative to the pmirLAAD parent, serine at position 98 of the mutant is mutated into alanine, and threonine at position 105 of the mutant is mutated into alanine to obtain a mutant S98A/T105A.

In one implementation, relative to the pmirLAAD parent, serine at position 98 of the mutant is mutated into alanine, threonine at position 105 of the mutant is mutated into alanine, and serine at position 106 of the mutant is mutated into alanine to obtain a mutant S98A/T105A/S106A.

In one implementation, relative to the pmirLAAD parent, serine at position 98 of the mutant is mutated into alanine, threonine at position 105 of the mutant is mutated into alanine, serine at position 106 of the mutant is mutated into alanine, and threonine at position 341 of the mutant is mutated into alanine to obtain a mutant S98A/T105A/S106A/L341A.

In one implementation, amino acid sequences of the mutants S98A, T105A, S106A, L341A, S98A/T105A, S98A/T105A/S106A and S98A/T105A/S106A/L341A are respectively shown in SEQ ID NO: 3, SEQ ID NO: 5, SEQ ID NO: 7, SEQ ID NO: 9, SEQ ID NO: 11, SEQ ID NO: 13 and SEQ ID NO: 15.

The disclosure provides a gene encoding the mutant. Nucleotide sequences of the genes encoding the mutants S98A, T105A, S106A, L341A, S98A/T105A, S98A/T105A/S106A and S98A/T105A/S106A/L341A are respectively shown in SEQ ID NO:4, SEQ ID NO:6, SEQ ID NO:8, SEQ ID NO:10, SEQ ID NO:12, SEQ ID NO:14 and SEQ ID NO:16.

The disclosure provides a recombinant plasmid containing the gene of the mutant, and the recombinant plasmid uses a pET series vector, a pRSFDuet series vector or a pGEX series vector as an expression vector.

The disclosure provides a method for obtaining the pmirLAAD mutant, and the method includes:
(1) determining a mutant site on the basis of the amino acid sequence of L-amino acid deaminase pmirLAAD of *Proteus mirabilis*; designing primers for site-saturation mutation and site-directed mutation, and performing site-directed mutation by using a vector carrying a gene of the L-amino acid deaminase pmirLAAD as a template; and constructing a recombinant plasmid containing the mutant;
(2) transforming the mutant plasmid into a host cell; and
(3) selecting a positive clone, and performing fermentation culture and induction to obtain a protein of the pmirLAAD mutant for subsequent transformation experiments.

In one implementation, the host cell is *E. coli* BL21 (DE3).

The disclosure provides a recombinant bacterium, and the recombinant bacterium expresses the mutant.

In one implementation, the recombinant bacterium uses *Bacillus subtilis* or *E. coli* as a host.

The disclosure provides a method for producing α-ketoisovaleric acid. According to the method, the recombinant bacterium is used to catalyze L-valine to obtain the α-ketoisovaleric acid.

In one implementation, the host bacterium is added to a transformation system containing 100-200 g/L L-valine, and a reaction is performed under conditions of the ventilation volume of 1-5 vvm for 22-26 h.

In one implementation, the reaction is performed under conditions of pH 8.5-9.5, 25-35° C. and the ventilation volume of 1-2 vvm for 22-25 h.

In one implementation, the final concentration of the host bacterium in the system is 10-30 g/L.

In one implementation, the final concentration of the host bacterium in the system is 10-15 g/L.

The disclosure provides a method for producing α-ketoisovaleric acid. According to the method, L-valine is used as a reaction substrate, the mutant is added to a reaction system, and the reaction is performed under conditions of pH 7.5-9.5, 20-40° C. and the ventilation volume of 1-5 vvm for 22-26 h.

In one implementation, the reaction is performed under conditions of pH 8.5-9.5, 25-35° C. and the ventilation volume of 1-2 vvm for 22-25 h.

The disclosure provides application of the mutant, or the gene encoding the mutant or the recombinant plasmid in preparation of α-ketoisovaleric acid or in increasing the yield of α-ketoisovaleric acid in the fields of food, medicines and chemical industry.

The disclosure provides application of the recombinant bacterium or the method for preparing α-ketoisovaleric acid in preparation of α-ketoisovaleric acid in the fields of food, medicines and chemical industry.

Beneficial effects: the disclosure constructs an L-amino acid deaminase mutant and a preparation method thereof for catalyzing production of α-ketoisovaleric acid. Compared with the control, the catalytic efficiency (1.61 mM$^{-1}$·min$^{-1}$) and the product inhibition constant (5.4 mM) of the disclosure are respectively increased by 5.2 times and 5.7 times. The production capacity per unit of catalyst is increased, and the production cost is effectively reduced. Besides, the reaction solution uses only water as a catalytic medium, and thus, has the advantages of mild reaction conditions, simple operation, easy separation, environmental friendliness and the like. The technique is simple and convenient to control, and is easy for popularization and application. When the mutant obtained in the disclosure uses L-valine as a substrate in a 3 L fermentor, the yield of the α-ketoisovaleric acid can reach 96.5 g/L, and the transformation rate is greater than 97%. The yield is currently the highest yield, thereby accelerating the industrialization process of the production of α-ketoisovaleric acid by the enzymatic transformation method.

BRIEF DESCRIPTION OF FIGURES

FIG. 1 is a graph showing the relation between the whole-cell catalyst concentration and the α-ketoisovaleric acid yield.

DETAILED DESCRIPTION

Gene source: a gene of a biological enzyme pmirLAAD involved in the disclosure is derived from *Proteus mirabilis*, pET28a(+) plasmids are purchased from Novagen (Madison, WI, U.S.A.), and restriction endonuclease, T4 DNA ligase, primeSTAR and the like are purchased from TaKaRa (Dalian, China). Standard samples are purchased from SIGMA. pmirLAAD mutants are all obtained by molecular modification, and the rest reagents are all purchased from the market.

LB medium: 10 g of peptone, 5 g of yeast powder, 10 g of sodium chloride, and distilled water to a volume of 1 L.

Fermentation medium: (TB medium): 12 g of peptone, 24 g of yeast extract, 4 mL of glycerol, 2.31 g of potassium dihydrogen phosphate, 16.42 g of dipotassium hydrogen phosphate, and distilled water to a volume of 1 L.

Preparation of sample for determining α-ketoisovaleric acid content by HPLC: 1 mL of a transformed transformation solution is centrifuged at 12000 rpm for 5 min, the supernatant is diluted and filtered through a 0.45 µm filtration membrane, and the filtrate is for liquid chromatography.

Determination of α-ketoisovaleric acid content by HPLC: a waters high performance liquid chromatograph (equipped with a UV-visible detector) and a Bio-Rad Aminex HPX-87H (300×7.8 mm, 9 µm) chromatographic column are used, and the mobile phase is dilute sulfuric acid with the concentration of 2.5 mmol/L. The mobile phase is filtered through a 0.22 µm filtration membrane; the filtrate is subjected to ultrasonic degassing; and detection is performed at the flow rate of 0.6 mL/min, the column temperature of 35° C. and the ultraviolet detection wavelength of 210 nm.

Example 1: Construction and Screening of Single Mutants (1) Construction of mutants: primers for mutant sites at position 98, position 105, position 106 and position 341 were designed, as shown in Table 1. The primers were constructed by full plasmid PCR.

TABLE 1

Sequences of mutation primers

| Primer | Sequence (5'-3') | |
|---|---|---|
| S98-S | GGCCGTGCATACNNKCAAATTATTAGT | SEQ ID NO: 17 |
| S98-A | ACTAATAATTTGMNNGTATGCACGGCC | SEQ ID NO: 18 |
| T105-S | ATTAGTTACCAANNKTCGCCAGAAATC | SEQ ID NO: 19 |
| T105-A | GATTTCTGGCGAMNNTTGGTAACTAAT | SEQ ID NO: 20 |
| S106-S | AGTTACCAAACANNKCCAGAAATCTTC | SEQ ID NO: 21 |
| S106-A | GAAGATTTCTGGMNNTGTTTGGTAACT | SEQ ID NO: 22 |
| L341-S | GGTGGCGGAGAGNNKCCGTTGGAATTC | SEQ ID NO: 23 |
| L341-A | GAATTCCAACGGMNNCTCTCCGCCACC | SEQ ID NO: 24 |

Construction of reaction PCR amplification system: PrimSTAR enzyme 0.5 µL, 5×PrimeSTAR Buffer 10 µL, dNTP 4 µL, two primers for each mutation site 1 µL each, template (nucleotide sequence of pmirLAAD) 4 µL, and water 32.5 µL. Reaction conditions: (1) 94° C. for 3 min; (2) 98° C. for 10 s; (3) 55° C. for 30 s; (4) 72° C. for 3 min; (5) 29 cycles of steps (2)-(4); (6) 72° C. for 5 min; (7) holding at 12° C.

The above reaction system was incubated at 37° C. for 3 h to digest the plasmid template (the digestion system was: Dpnl 0.5 µL, the above reaction PCR product 45 µL, and 10×T Buffer 5 µL). After the completion of the digestion, the obtained digestion product was introduced into *E. coli* BL21 competent cells by a chemical transformation method. The chemical transformation method included the following specific steps:

1) 10 µl of a homologous recombination product was introduced into 100 µl of BL21 competent cells.
2) An ice bath was applied for 15-30 min.
3) A 42° C. water bath was applied for heat shock for 90 s, and the mixture was quickly placed in ice and allowed to stand in an ice bath for 3-5 min.
4) 800 µl of a non-resistant LB medium was added, and the mixture was uniformly mixed and cultured at 37° C. at 200 rpm for 1 h.
5) The mixture was centrifuged at 5000 rpm for 2 min to collect the bacterium.
6) The supernatant was removed, and the remaining 100-200 µL of solution was uniformly mixed by blowing-suction, coated on a resistant plate containing 0.05 mg/mL kanamycin, and cultured at the constant temperature of 37° C. for about 12 h.

7) A monoclonal antibody was picked and placed in a resistant LB containing 0.05 mg/mL kanamycin. After 12 h of culture at 200 rpm at the constant temperature of 37° C., the product was sent to a company for sequencing. Those that were correctly sequenced are positive transformants (mutant strains). The mutation sites were respectively a mutation of S at position 98 to A, a mutation of T at position 105 to A, a mutation of S at position 106 to A, and a mutation of L at position 341 to A.

(2) Shake flask screening of single mutants: The obtained 4 mutant strains and a strain containing wild-type L-amino acid deaminase were respectively inoculated into an LB seed medium, and cultured at 200 rpm at 37° C. for about 10 h. The products were respectively inoculated into a shake flask fermentation medium with the inoculum size of 5% of the medium by volume, and cultured at 200 rpm at 37° C. until $OD_{600}$ was about 0.8. IPTG with the final concentration of 0.04 mmol/L was added for induction, and the induction was performed at 200 rpm at 25° C. for 14 h. The product was centrifuged at 6000 rpm for 8 min to collect bacterial cells. The bacterial cells collected by centrifugation were used for later transformation experiments.

Transformation conditions: transformation temperature 25° C., reaction pH 8.0, and transformation time 24 h.

The yield of α-ketoisovaleric acid of the transformation solution after the completion of the transformation was determined by HPLC. The results are shown in Table 2. Finally, S98A produced α-ketoisovaleric acid at the highest yield.

TABLE 2

Results of shake flask screening of single mutants

| Mutant | α-ketoisovaleric acid (g/L) |
|---|---|
| WT | 39.8 |
| PmirLAAD$^{S98A}$ | 46.9 |
| PmirLAAD$^{T105A}$ | 44.6 |
| PmirLAAD$^{S106A}$ | 44.9 |
| PmirLAAD$^{L341A}$ | 43.6 |

Example 2: Construction and Screening of Double, Triple and Quadruple Mutants (1) Construction of double mutants: On the basis of the mutant PmirLAAD$^{S98A}$, mutation primers T105A-S and T105A-A, S106A-S and S106A-A, as well as L341A-S and L341A-A were used to respectively construct double mutants. On the basis of the mutant PmirLAAD$^{T105A}$, mutation primers S106A*-S and S106A*-A, as well as L341A-S and L341A-A were used to respectively construct double mutants. On the basis of the mutant PmirLAAD$^{S106A}$, mutation primers L341A-S and L341A-A were used (Table 3). Double mutants were constructed by full plasmid PCR. For the specific implementation manner, reference can be made to step (1) in Example 1. 6 double mutants PmirLAAD$^{S98A/T105A}$, PmirLAAD$^{S98A/S106A}$, PmirLAAD$^{S98A/L341A}$, PmirLAAD$^{T105A/S106A}$, PmirLAAD$^{T105A/L341A}$ and PmirLAAD$^{S106A/L341A}$ were obtained.

TABLE 3

Sequences of mutation primers of double mutants

| Primer | Sequence (5'-3') | |
|---|---|---|
| T105A-S | ATTAGTTACCAAGCCTCGCCAGAAATC | SEQ ID NO: 25 |
| T105A-A | GATTTCTGGCGAGGCTTGGTAACTAAT | SEQ ID NO: 26 |
| S106A-S | AGTTACCAAACAGCACCAGAAATCTTC | SEQ ID NO: 27 |
| S106A-A | GAAGATTTCTGGTGCTGTTTGGTAACT | SEQ ID NO: 28 |
| L341A-S | GGTGGCGGAGAGGCACCGTTGGAATTC | SEQ ID NO: 29 |
| L341A-A | GAATTCCAACGGTGCCTCTCCGCCACC | SEQ ID NO: 30 |
| S106A*-S | AGTTACCAAGCCGCACCAGAAATCTTC | SEQ ID NO: 31 |
| S106A*-A | GAAGATTTCTGGTGCGGCTTGGTAACT | SEQ ID NO: 32 |

(2) Screening of double mutants: For the specific implementation manner, reference can be made to step (3) in Example 3. The results are shown in Table 4. Finally, S98A/T105A produced α-ketoisovaleric acid at the highest yield.

TABLE 4

Results of shake flask screening of double mutants

| Mutant | α-ketoisovaleric acid (g/L) |
|---|---|
| PmirLAAD$^{S98A/T105A}$ | 52.6 |
| PmirLAAD$^{S98A/S106A}$ | 50.9 |
| PmirLAAD$^{S98A/L341A}$ | 51.5 |
| PmirLAAD$^{T105A/S106A}$ | 49.4 |
| PmirLAAD$^{T105A/L341A}$ | 47.1 |
| PmirLAAD$^{S106A/L341A}$ | 46.5 |

(3) Construction of triple mutants: On the basis of the mutant PmirLAAD$^{S98A/T105A}$, mutation primers S106A*-S and S106A*-A, as well as L341A-S and L341A-A were used to respectively construct triple mutants. On the basis of the mutants PmirLAAD$^{S98A/S106A}$ and PmirLAAD$^{T105A/S106A}$, mutation primers L341A-S and L341A-A were used to respectively construct triplet mutants (Table 4). Triple mutants were constructed by full plasmid PCR. For the specific implementation manner, reference can be made to step (1) in Example 3. Four triple mutants PmirLAAD$^{S98A/T105A/S106A}$, PmirLAAD$^{S98A/T105A/L341A}$, PmirLAAD$^{S98A/S106A/L341A}$ and PmirLAAD$^{T105A/S106A/L341A}$ were obtained.

(4) Screening of triple mutants: For the specific implementation manner, reference can be made to step (2) in Example 1. The results are shown in Table 5. Finally, S98A/T105A/S106A produced α-ketoisovaleric acid at the highest yield.

TABLE 5

Results of shake flask screening of triple mutants

| Mutant | α-ketoisovaleric acid (g/L) |
|---|---|
| PmirLAAD$^{S98A/T105A/S106A}$ | 60.6 |
| PmirLAAD$^{S98A/T105A/L341A}$ | 56.1 |
| PmirLAAD$^{S98A/S106A/L341A}$ | 53.5 |
| PmirLAAD$^{T105A/S106A/L341A}$ | 59.6 |

(5) Construction of quadruple mutants: On the basis of the mutant PmirLAAD$^{S98A/T105A/S106A}$, L341A was mutated: the mutant PmirLAAD$^{S98A/T105A/S106A}$ was used as a template, mutation primers L341A-S and L341A-A (Table 3) were used to perform full plasmid PCR, and the PCR product was digested. The PCR system and the digestion system were the same as those in Example 3.

Example 3: Determination of Kinetic Parameters and Product Inhibition Constants of Parent Enzyme and Mutants In order to evaluate the mutants, kinetic parameters of the mutant parent PmirLAAD$^{WT}$ and the mutants PmirLAAD$^{M1}$, PmirLAAD$^{M2}$, PmirLAAD$^{M3}$ and PmirLAAD$^{M4}$ at 25° C. were determined in the disclosure.

$k_{cat}/K_m$ was calculated based on the initial rate of α-ketoisovaleric acid produced from hydrolyzed L-valine substrates with different concentrations determined at 25° C. Product inhibition of the parent enzyme and the mutants was determined by a product inhibition constant determination experiment in the transformation process. A PmirLAAD$^{WT}$ parent enzyme strain and mutant strains were respectively added to a reaction solution with the final concentration of wet cells of 10 g/L. 60 mM L-valine was used as the substrate, 10-100 mM α-ketoisovaleric acid was added to the transformation system, the initial reaction rate $V_0$ was determined after about 30 min of reaction, the maximum reaction rate $V_{max}$ was determined after about 2 h of reaction, and the product inhibition constant $K_{PI}$ was calculated according to the following formula:

$$V_0 = \frac{V_{max}[S]}{K_m\left(1 + \frac{[P]}{K_{PI}}\right) + [S]}$$

$V_0$: initial reaction rate, $V_{max}$: maximum reaction rate, $K_m$: Michaelis constant, [S]: substrate concentration, [P]: product concentration, $K_{PI}$: product inhibition constant.

As shown in Table 6, at 25° C., compared with the parent enzyme, the $K_{cat}/K_m$ value of all the mutants is increased. The $k_{cat}/K_m$ value of the mutant PmirLAAD M4 is increased by 5.2 times, resulting in greater catalytic efficiency of PmirLAAD. Accordingly, compared with the parent enzyme, the product inhibition constant of the mutants each is increased. The product inhibition constant of the mutant PmirLAAD M4 (hereinafter referred to as M4 strain) is increased by 5.7 times.

kanamycin, and cultured at 200 rpm at 37° C. for 10-12 h. The product was inoculated into a TB medium with the inoculum size of the volume ratio of 5%, and cultured at 200 rpm at 37° C. until $OD_{600}$ was 3. IPTG with the final concentration of 0.04 mmol/L was added for induction, and the induction was performed at 25° C. for 14 h. The product was centrifuged at 6,000×g for 8 min to collect cells. The cells were placed in a −40° C. refrigerator for transformation.

(1) Influences of Different Whole-Cell Catalyst Concentrations on α-Ketoisovaleric Acid Concentration Preparation of transformation reaction system in fermentor: L-valine was dissolved in a certain amount of Tris-HCl buffer, the L-valine solution was poured into a fermentor (such that the final concentration of the L-valine in the reaction system was 160 g/L), the temperature was adjusted to 25° C., and the rotation speed was 300 rpm. 10 g, 15 g, 20 g, 25 g and 30 g of mutant wet bacterial cells (that is, whole-cell catalyst) were also dissolved uniformly in a buffer. After the temperature of the transformation solution increased to 25° C., the dissolved bacterial solution was poured into the fermentor (the whole-cell catalyst concentrations were respectively 10 g/L, 15 g/L, 20 g/L, 25 g/L and 30 g/L).

A transformation reaction was performed under conditions of 25° C., 600 rpm and the ventilation volume of 1 vvm, and the total volume after the transformation reaction was 1 L.

After the completion of the transformation reaction, a part of the transformation solution was centrifuged at 12,000×g for 15 min, the supernatant was filtered through a 0.22 μm microfiltration membrane, and the filtrate was analyzed by HPLC. The results are shown in FIG. 1. When the catalyst concentration was increased from 10 g/L to 30 g/L, the α-ketoisovaleric acid concentration was increased from 76.7 g/L to 154.3 g/L. However, the product/catalyst ratio was decreased from 7.6 g/g to 5.1 g/g. Considering the industrial demands for high yield and low catalyst (bacterial cell) consumption, the whole-cell catalyst concentration of 10 g/L had higher α-ketoisovaleric acid concentration and high product/catalyst ratio (that is, the capacity for producing α-ketoisovaleric acid per unit of bacterial cells) of 7.6 g/g at the same time, and was used for transformation experiments.

(2) Influences of Different Transformation Reaction pH Values on α-Ketoisovaleric Acid Concentration

TABLE 6

Kinetic parameters of PmirLAAD parent enzyme and mutants thereof

| Mutant | $k_{cat}/K_m$ (mM$^{-1}$·min$^{-1}$) | Times of change | $K_{PI}$ (mM) | Times of change |
|---|---|---|---|---|
| PmirLAAD$^{WT}$ | 0.26 | 1 | 0.8 ± 0.6 | 1 |
| PmirLAAD$^{M1}$ (PmirLAAD$^{S98A}$) | 0.75 | 2.9 | 2.08 ± 0.9 | 2.6 |
| PmirLAAD$^{M2}$ (PmirLAAD$^{S98A/T105A}$) | 0.98 | 3.8 | 3.12 ± 0.4 | 3.9 |
| PmirLAAD$^{M3}$ (PmirLAAD$^{S98A/T105A/S106A}$) | 1.25 | 4.8 | 3.7 ± 0.3 | 4.6 |
| PmirLAAD$^{M4}$ (PmirLAAD$^{S98A/T105A/S106A/L341A}$) | 1.61 | 6.2 | 5.4 ± 0.2 | 6.7 |

Example 4: Production of α-Ketoisovaleric Acid from L-Valine by 1 L System Level Optimization The correctly sequenced mutant M4 strain on the plate was inoculated into a resistant LB containing 0.05 mg/mL The specific steps were the same as those in (1). The whole-cell catalyst concentration was controlled at 10 g/L, the L-valine concentration was controlled at 100 g/L, the ventilation volume was 1 vvm, and the pH in the transformation reaction process was respectively controlled at 7.5, 8.0, 8.5, 9.0 and 9.5. The results are shown in Table 7. A weak acid or weak alkaline pH was more suitable for synthesis of α-ketoisovaleric acid, and therefore, the transformation pH was controlled at 8.5-9.0. At this time, the α-ketoisovaleric acid concentration was 78.9 g/L

TABLE 7

Optimization results of transformation pH

| pH | 7.5 | 8.0 | 8.5 | 9.0 | 9.5 |
|---|---|---|---|---|---|
| A-ketoisovaleric acid (g/L) | 61.7 | 67.1 | 78.9 | 74.3 | 70.4 |

(3) Influences of Different Transformation Reaction Temperature on α-Ketoisovaleric Acid Concentration The specific steps were the same as those in (1). The transformation pH was controlled at 8.5, the whole-cell catalyst concentration was controlled at 10 g/L, the ventilation volume was 1 vvm, and the temperature in the transformation reaction process was respectively controlled at 20° C., 25° C., 30° C., 35° C. and 40° C. The results are shown in Table 8. The temperature of 30° C. was more suitable for synthesis of α-ketoisovaleric acid, and therefore, the transformation temperature was controlled at about 30° C. At this time, the α-ketoisovaleric acid concentration was 78.9 g/L.

TABLE 8

Optimization results of transformation temperature

| Temperature ° C. | 20 | 25 | 30 | 35 | 40 |
|---|---|---|---|---|---|
| A-ketoisovaleric acid (g/L) | 71.2 | 79.1 | 88.9 | 81.3 | 76.4 |

(4) Influences of Different Transformation Reaction Ventilation Volumes on α-Ketoisovaleric Acid Concentration The specific steps were the same as those in (1). The transformation pH was controlled at 8.5, the whole-cell catalyst concentration was controlled at 10 g/L, the temperature was controlled at 30° C., and the ventilation volume was controlled at 1 vvm, 1.5 vvm, 2 vvm, 2.5 vvm and 3 vvm. The results are shown in Table 9. The ventilation volume of 1.5 vvm was more suitable for synthesis of α-ketoisovaleric acid, and therefore, the ventilation volume was controlled at about 1.5 vvm. At this time, the α-ketoisovaleric acid concentration was 96.5 g/L.

TABLE 9

Optimization results of transformation ventilation volume

| Ventilation volume vvm | 1 | 1.5 | 2 | 2.5 | 3 |
|---|---|---|---|---|---|
| A-ketoisovaleric acid (g/L) | 88.9 | 96.5 | 87.4 | 80.3 | 75.2 |

Comparative Example 1

For the specific implementation manner, reference can be made to Example 4. The difference is that the mutant M4 strain was replaced the wild type WT strain for fermentation and transformation experiments. After the completion of the transformation, a part of the transformation solution was centrifuged at 12,000×g for 15 min, the supernatant was filtered through a 0.22 μm microfiltration membrane, and the filtrate was analyzed by HPLC. HPLC chromatogram results showed that the yield of α-ketoisovaleric acid was 40 g/L, and the transformation rate was 40.3%.

Although the disclosure has been disclosed as above in the preferred examples, it is not intended to limit the disclosure. Anyone familiar with this technology can make various changes and modifications without departing from the spirit and scope of the disclosure. Therefore, the protection scope of the disclosure should be as defined in the claims.

What is claimed is:

1. An L-amino acid deaminase mutant, comprising the amino acid sequence having all of SEQ ID NO: 1 except for a mutation in one or more of amino acids at position 98, position 105, position 106 or position 341,
wherein the mutation
serine 98 to alanine, threonine 105 to alanine, serine 106 to alanine, and leucine 341 to alanine, and
wherein the L-amino acid deaminase mutant catalyzes conversion of L-valine to α-ketoisovaleric acid and possesses a $k_{cat}/K_m$ value at 25° C. that is at least 5-fold higher than the $k_{cat}/K_m$ value of a corresponding wild type L-amino acid deaminase.

2. A recombinant bacterium, comprising the L-amino acid deaminase mutant of claim 1.

3. The recombinant bacterium according to claim 2, wherein the bacterium is *Bacillus subtilis* or *Escherichia coli*.

4. A method of producing α-ketoisovaleric acid, comprising:
culturing the recombinant bacterium of claim 2 in the presence of L-valine under conditions that cause expression of the L-amino acid deaminase mutant.

5. The method according to claim 4, wherein culturing is performed in culture medium comprising 100 g/L to 200 g/L L-valine, and at a ventilation volume of 1 vvm to 5 vvm for 22 hours to 26 hours.

6. The method according to claim 5, wherein a final concentration of the recombinant bacterium is 10 g/L to 30 g/L.

7. The method according to claim 6, wherein culturing is performed at 20° C. to 40° C. and at a pH of 7.5 to 9.5.

8. The L-amino acid deaminase mutant of claim 1, wherein the mutation is serine 98 to alanine.

* * * * *

SEQUENCE LISTING

```
<160> NUMBER OF SEQ ID NOS: 32

<210> SEQ ID NO 1
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 1

Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
                20                  25                  30

Lys Phe Val Glu Ala Lys Ser Arg Ala Ser Phe Val Glu Gly Thr Gln
            35                  40                  45

Gly Ala Leu Pro Lys Glu Ala Asp Val Val Ile Ile Gly Ala Gly Ile
        50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

```
Tyr Ser Gln Ile Ile Ser Tyr Gln Thr Ser Pro Glu Ile Phe Pro Leu
            100                 105                 110
His His Tyr Gly Lys Ile Leu Trp Arg Gly Met Asn Glu Lys Ile Gly
        115                 120                 125
Ala Asp Thr Ser Tyr Arg Thr Gln Gly Arg Val Glu Ala Leu Ala Asp
    130                 135                 140
Glu Lys Ala Leu Asp Lys Ala Gln Ala Trp Ile Lys Thr Ala Lys Glu
145                 150                 155                 160
Ala Ala Gly Phe Asp Thr Pro Leu Asn Thr Arg Ile Ile Lys Gly Glu
                165                 170                 175
Glu Leu Ser Asn Arg Leu Val Gly Ala Gln Thr Pro Trp Thr Val Ala
            180                 185                 190
Ala Phe Glu Glu Asp Ser Gly Ser Val Asp Pro Glu Thr Gly Thr Pro
        195                 200                 205
Ala Leu Ala Arg Tyr Ala Lys Gln Ile Gly Val Lys Ile Tyr Thr Asn
    210                 215                 220
Cys Ala Val Arg Gly Ile Glu Thr Ala Gly Gly Lys Ile Ser Asp Val
225                 230                 235                 240
Val Ser Glu Lys Gly Ala Ile Lys Thr Ser Gln Val Val Leu Ala Gly
                245                 250                 255
Gly Ile Trp Ser Arg Leu Phe Met Gly Asn Met Gly Ile Asp Ile Pro
            260                 265                 270
Thr Leu Asn Val Tyr Leu Ser Gln Gln Arg Val Ser Gly Val Pro Gly
        275                 280                 285
Ala Pro Arg Gly Asn Val His Leu Pro Asn Gly Ile His Phe Arg Glu
    290                 295                 300
Gln Ala Asp Gly Thr Tyr Ala Val Ala Pro Arg Ile Phe Thr Ser Ser
305                 310                 315                 320
Ile Val Lys Asp Ser Phe Leu Leu Gly Pro Lys Phe Met His Leu Leu
                325                 330                 335
Gly Gly Gly Glu Leu Pro Leu Glu Phe Ser Ile Gly Glu Asp Leu Phe
            340                 345                 350
Asn Ser Phe Lys Met Pro Thr Ser Trp Asn Leu Asp Glu Lys Thr Pro
        355                 360                 365
Phe Glu Gln Phe Arg Val Ala Thr Ala Thr Gln Asn Thr Gln His Leu
    370                 375                 380
Asp Ala Val Phe Gln Arg Met Lys Thr Glu Phe Pro Val Phe Glu Lys
385                 390                 395                 400
Ser Glu Val Val Glu Arg Trp Gly Ala Val Val Ser Pro Thr Phe Asp
                405                 410                 415
Glu Leu Pro Ile Ile Ser Glu Val Lys Glu Tyr Pro Gly Leu Val Ile
            420                 425                 430
Asn Thr Ala Thr Val Trp Gly Met Thr Glu Gly Pro Ala Ala Gly Glu
        435                 440                 445
Val Thr Ala Asp Ile Val Met Gly Lys Lys Pro Val Ile Asp Pro Thr
    450                 455                 460
Pro Phe Ser Leu Asp Arg Phe Lys Lys
465                 470
```

<210> SEQ ID NO 2
<211> LENGTH: 1422
<212> TYPE: DNA
<213> ORGANISM: Artificial Sequence
<220> FEATURE:
<223> OTHER INFORMATION: Synthetic DNA

<400> SEQUENCE: 2

```
atgaacattt caaggagaaa gctactttta ggtgttggtg ctgcgggcgt tttagcaggt      60
ggtgcggctt tagttccaat ggttcgccgt gacggcaaat ttgtggaagc taaatcaaga     120
gcatcatttg ttgaaggtac gcaagggggct cttcctaaag aagcagatgt agtgattatt    180
ggtgccggta ttcaagggat catgaccgct attaaccttg ctgaacgtgg tatgagtgtc     240
actatcttag aaaagggtca gattgccggt gagcaatcag gccgtgcata cagccaaatt    300
attagttacc aaacatcgcc agaaatcttc ccattacacc attatgggaa atattatgg     360
cgtggcatga atgagaaaat tggtgcggat accagtatc gtactcaagg tcgtgtagaa     420
gcgctggcag atgaaaaagc attagataaa gctcaagcgt ggatcaaaac agctaaagaa    480
gcggcaggtt ttgatacacc attaaatact cgcatcatta aggtgaaga gctatcaaat     540
cgcttagtcg gtgctcaaac gccatggact gttgctgcat ttgaagaaga ttcaggctct    600
gttgatcctg aaacaggcac acctgcactc gctcgttatg ccaaacaaat cggtgtgaaa    660
atttatacca actgtgcagt aagaggtatt gaaactgcgg tggtaaaaat ctctgatgtg    720
gtgagtgaga aaggggcgat taaaacgtct caagttgtac tcgctggggg tatctggtcg    780
cgtttattta tgggcaatat gggtattgat atcccaacgc tcaatgtata tctatcacaa    840
caacgtgtct caggggttcc tggtgcacca cgtggtaatg tgcatttacc taatggtatt    900
catttccgcg aacaagcgga tggtacttat gccgttgcac cacgtatctt tacgagttca    960
atagtcaaag atagcttcct gctagggcct aaatttatgc acttattagg tggcggagag   1020
ttaccgttgg aattctctat tggtgaagat ctatttaatt catttaaaat gccgacctct   1080
tggaatttag atgaaaaaac accattcgaa caattccgag ttgccacggc aacacaaaat   1140
acgcaacact tagatgctgt tttccaaaga atgaaaacag aattcccagt atttgaaaaa   1200
tcagaagttg ttgaacgttg gggtgccgtt gtgagtccaa catttgatga attacctatc   1260
atttctgagg tcaaagaata cccaggctta gtgattaaca cggcaacagt gtggggtatg   1320
acagaaggcc cggcagcggg tgaagtgacc gctgatattg tcatgggcaa gaaacctgtt   1380
attgatccaa cgccgtttag tttggatcgt tttaagaagt aa                       1422
```

<210> SEQ ID NO 3
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 3

```
Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Ile Gly Ala Gly Ile
    50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

```
Tyr Ala Gln Ile Ile Ser Tyr Gln Thr Ser Pro Glu Ile Phe Pro Leu
                100                 105                 110

His His Tyr Gly Lys Ile Leu Trp Arg Gly Met Asn Glu Lys Ile Gly
            115                 120                 125

Ala Asp Thr Ser Tyr Arg Thr Gln Gly Arg Val Glu Ala Leu Ala Asp
        130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
210                 215                 220

Cys Ala Val Arg Gly Ile Glu Thr Ala Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
450                 455                 460

Pro Phe Ser Leu Asp Arg Phe Lys Lys
465                 470

<210> SEQ ID NO 4
<211> LENGTH: 1422
<212> TYPE: DNA
<213> ORGANISM: Artificial Sequence
<220> FEATURE:
<223> OTHER INFORMATION: Synthetic DNA
```

<400> SEQUENCE: 4

```
atgaacattt caaggagaaa gctacttta ggtgttggtg ctgcgggcgt tttagcaggt        60
ggtgcggctt tagttccaat ggttcgccgt gacggcaaat ttgtggaagc taaatcaaga       120
gcatcatttg ttgaaggtac gcaaggggct cttcctaaag aagcagatgt agtgattatt       180
ggtgccggta ttcaagggat catgaccgct attaaccttg ctgaacgtgg tatgagtgtc       240
actatcttag aaaagggtca gattgccggt gagcaatcag gccgtgcata cgcacaaatt       300
attagttacc aaacatcgcc agaaatcttc ccattacacc attatgggaa atattatgg        360
cgtggcatga atgagaaaat tggtgcggat accagttatc gtactcaagg tcgtgtagaa       420
gcgctggcag atgaaaaagc attagataaa gctcaagcgt ggatcaaaac agctaaagaa       480
gcggcaggtt ttgatacacc attaaatact cgcatcatta aggtgaaga gctatcaaat        540
cgcttagtcg gtgctcaaac gccatggact gttgctgcat ttgaagaaga ttcaggctct       600
gttgatcctg aaacaggcac acctgcactc gctcgttatg ccaaacaaat cggtgtgaaa       660
atttatacca actgtgcagt aagaggtatt gaaactgcgg gtggtaaaat ctctgatgtg       720
gtgagtgaga aaggggcgat taaaacgtct caagttgtac tcgctggggg tatctggtcg       780
cgtttattta tgggcaatat gggtattgat atcccaacgc tcaatgtata tctatcacaa       840
caacgtgtct caggggttcc tggtgcacca cgtggtaatg tgcatttacc taatggtatt       900
catttccgcg aacaagcgga tggtacttat gccgttgcac cacgtatctt tacgagttca       960
atagtcaaag atagcttcct gctagggcct aaatttatgc acttattagg tggcggagag      1020
ttaccgttgg aattctctat tggtgaagat ctatttaatt catttaaaat gccgacctct      1080
tggaatttag atgaaaaaac accattcgaa caattccgag ttgccacggc aacacaaaat      1140
acgcaacact agatgctgt tttccaaaga atgaaaacag aattcccagt atttgaaaaa       1200
tcagaagttg ttgaacgttg gggtgccgtt gtgagtccaa catttgatga attacctatc      1260
atttctgagg tcaaagaata cccaggctta gtgattaaca cggcaacagt gtgggtatg       1320
acagaaggcc cggcagcggg tgaagtgacc gctgatattg tcatgggcaa gaaacctgtt      1380
attgatccaa cgccgtttag tttggatcgt tttaagaagt aa                         1422
```

<210> SEQ ID NO 5
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 5

```
Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
                20                  25                  30

Lys Phe Val Glu Ala Lys Ser Arg Ala Ser Phe Val Glu Gly Thr Gln
            35                  40                  45

Gly Ala Leu Pro Lys Glu Ala Asp Val Val Ile Ile Gly Ala Gly Ile
        50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

```
Tyr Ser Gln Ile Ile Ser Tyr Gln Ala Ser Pro Glu Ile Phe Pro Leu
            100                 105                 110

His His Tyr Gly Lys Ile Leu Trp Arg Gly Met Asn Glu Lys Ile Gly
        115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470
```

<210> SEQ ID NO 6
<211> LENGTH: 1422
<212> TYPE: DNA
<213> ORGANISM: Artificial Sequence
<220> FEATURE:
<223> OTHER INFORMATION: Synthetic DNA

<400> SEQUENCE: 6

```
atgaacattt caaggagaaa gctactttta ggtgttggtg ctgcgggcgt tttagcaggt    60
ggtgcggctt tagttccaat ggttcgccgt gacggcaaat ttgtggaagc taaatcaaga   120
gcatcatttg ttgaaggtac gcaagggggct cttcctaaag aagcagatgt agtgattatt   180
ggtgccggta ttcaagggat catgaccgct attaaccttg ctgaacgtgg tatgagtgtc   240
actatcttag aaaagggtca gattgccggt gagcaatcag gccgtgcata cagccaaatt   300
attagttacc aagcctcgcc agaaatcttc ccattacacc attatgggaa aatattatgg   360
cgtggcatga atgagaaaat tggtgcggat accagttatc gtactcaagg tcgtgtagaa   420
gcgctggcag atgaaaaagc attagataaa gctcaagcgt ggatcaaaac agctaaagaa   480
gcggcaggtt ttgatacacc attaaatact cgcatcatta aggtgaagaa gctatcaaat   540
cgcttagtcg gtgctcaaac gccatggact gttgctgcat ttgaagaaga ttcaggctct   600
gttgatcctg aaacaggcac acctgcactc gctcgttatg ccaaacaaat cggtgtgaaa   660
atttatacca actgtgcagt aagaggtatt gaaactgcgg gtggtaaaat ctctgatgtg   720
gtgagtgaga aggggcgat taaaacgtct caagttgtac tcgctggggg tatctggtcg   780
cgtttattta tgggcaatat gggtattgat atcccaacgc tcaatgtata tctatcacaa   840
caacgtgtct caggggttcc tggtgcacca cgtggtaatg tgcatttacc taatggtatt   900
catttccgcg aacaagcgga tggtacttat gccgttgcac cacgtatctt tacgagttca   960
atagtcaaag atagcttcct gctagggcct aaatttatgc acttattagg tggcggagag  1020
ttaccgttgg aattctctat tggtgaagat ctatttaatt catttaaaat gccgacctct  1080
tggaatttag atgaaaaac accattcgaa caattccgag ttgccacggc aacacaaaat  1140
acgcaacact tagatgctgt tttccaaaga atgaaaacag aattcccagt atttgaaaaa  1200
tcagaagttg ttgaacgttg gggtgccgtt gtgagtccaa catttgatga attacctatc  1260
atttctgagg tcaaagaata cccaggctta gtgattaaca cggcaacagt gtggggtatg  1320
acagaaggcc cggcagcggg tgaagtgacc gctgatattg tcatgggcaa gaaacctgtt  1380
attgatccaa cgccgtttag tttggatcgt tttaagaagt aa                      1422
```

<210> SEQ ID NO 7
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 7

```
Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Ile Gly Ala Gly Ile
    50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

Tyr Ser Gln Ile Ile Ser Tyr Gln Thr Ala Pro Glu Ile Phe Pro Leu
            100                 105                 110

His His Tyr Gly Lys Ile Leu Trp Arg Gly Met Asn Glu Lys Ile Gly
        115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
                420                 425                 430

Asn Thr Ala Thr Val Trp Gly Met Thr Glu Gly Pro Ala Ala Gly Glu
            435                 440                 445

Val Thr Ala Asp Ile Val Met Gly Lys Lys Pro Val Ile Asp Pro Thr
        450                 455                 460

Pro Phe Ser Leu Asp Arg Phe Lys Lys
465                 470

<210> SEQ ID NO 8
<211> LENGTH: 1422
<212> TYPE: DNA
<213> ORGANISM: Artificial Sequence
<220> FEATURE:
<223> OTHER INFORMATION: Synthetic DNA

<400> SEQUENCE: 8

```
atgaacattt caaggagaaa gctactttta ggtgttggtg ctgcgggcgt tttagcaggt    60
ggtgcggctt tagttccaat ggttcgccgt gacggcaaat ttgtggaagc taaatcaaga   120
gcatcatttg ttgaaggtac gcaagggggct cttcctaaag aagcagatgt agtgattatt   180
ggtgccggta ttcaagggat catgaccgct attaaccttg ctgaacgtgg tatgagtgtc   240
actatcttag aaaagggtca gattgccggt gagcaatcag gccgtgcata cagccaaatt   300
attagttacc aaacagcacc agaaatcttc ccattacacc attatgggaa atattatgg    360
cgtggcatga atgagaaaat tggtgcggat accagttatc gtactcaagg tcgtgtagaa   420
gcgctggcag atgaaaaagc attagataaa gctcaagcgt ggatcaaaac agctaaagaa   480
gcggcaggtt ttgatacacc attaaatact cgcatcatta aggtgaagaa gctatcaaat   540
cgcttagtcg gtgctcaaac gccatggact gttgctgcat ttgaagaaga ttcaggctct   600
gttgatcctg aaacaggcac acctgcactc gctcgttatg ccaaacaaat cggtgtgaaa   660
atttatacca actgtgcagt aagaggtatt gaaactgcgg tggtaaaaat ctctgatgtg   720
gtgagtgaga aaggggcgat taaaacgtct caagttgtac tcgctggggg tatctggtcg   780
cgtttatttta tgggcaatat gggtattgat atcccaacgc tcaatgtata tctatcacaa   840
caacgtgtct caggggttcc tggtgcacca cgtggtaatg tgcatttacc taatggtatt   900
catttccgcg aacaagcgga tggtacttat gccgttgcac cacgtatctt tacgagttca   960
atagtcaaag atagcttcct gctagggcct aaatttatgc acttattagg tggcggagag  1020
ttaccgttgg aattctctat tggtgaagat ctatttaatt catttaaaat gccgacctct  1080
tggaattta atgaaaaaac accattcgaa caattccgag ttgccacggc aacacaaaat  1140
acgcaacact tagatgctgt tttccaaaga atgaaaacag aattcccagt attgaaaaa  1200
tcagaagttg ttgaacgttg gggtgccgtt gtgagtccaa catttgatga attacctatc  1260
atttctgagg tcaaagaata cccaggctta gtgattaaca cggcaacagt gtggggtatg  1320
acagaaggcc cggcagcggg tgaagtgacc gctgatattg tcatgggcaa gaaacctgtt  1380
attgatccaa cgccgtttag tttggatcgt tttaagaagt aa                    1422
```

<210> SEQ ID NO 9
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 9

```
Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
                20                  25                  30

Lys Phe Val Glu Ala Lys Ser Arg Ala Ser Phe Val Glu Gly Thr Gln
            35                  40                  45

Gly Ala Leu Pro Lys Glu Ala Asp Val Val Ile Ile Gly Ala Gly Ile
        50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

```
Tyr Ser Gln Ile Ile Ser Tyr Gln Thr Ser Pro Glu Ile Phe Pro Leu
            100                 105                 110

His His Tyr Gly Lys Ile Leu Trp Arg Gly Met Asn Glu Lys Ile Gly
        115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Ala Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470

<210> SEQ ID NO 10
<211> LENGTH: 1422
<212> TYPE: DNA
<213> ORGANISM: Artificial Sequence
<220> FEATURE:
<223> OTHER INFORMATION: Synthetic DNA
```

<400> SEQUENCE: 10

```
atgaacattt caaggagaaa gctacttta ggtgttggtg ctgcgggcgt tttagcaggt    60
ggtgcggctt tagttccaat ggttcgccgt gacggcaaat ttgtggaagc taaatcaaga   120
gcatcatttg ttgaaggtac gcaaggggct cttcctaaag aagcagatgt agtgattatt   180
ggtgccggta ttcaagggat catgaccgct attaaccttg ctgaacgtgg tatgagtgtc   240
actatcttag aaaagggtca gattgccggt gagcaatcag gccgtgcata cagccaaatt   300
attagttacc aaacatcgcc agaaatcttc ccattacacc attatgggaa atattatgg    360
cgtggcatga tgagaaaat tggtgcggat accagttatc gtactcaagg tcgtgtagaa    420
gcgctggcag atgaaaaagc attagataaa gctcaagcgt ggatcaaaac agctaaagaa   480
gcggcaggtt ttgatacacc attaaatact cgcatcatta aggtgaaga gctatcaaat    540
cgcttagtcg gtgctcaaac gccatggact gttgctgcat ttgaagaaga ttcaggctct   600
gttgatcctg aaacaggcac acctgcactc gctcgttatg ccaaacaaat cggtgtgaaa   660
atttatacca actgtgcagt aagaggtatt gaaactgcgg gtggtaaaat ctctgatgtg   720
gtgagtgaga aggggcgat taaaacgtct caagttgtac tcgctggggg tatctggtcg    780
cgtttattta tgggcaatat gggtattgat atcccaacgc tcaatgtata tctatcacaa   840
caacgtgtct caggggttcc tggtgcacca cgtggtaatg tgcatttacc taatggtatt   900
catttccgcg aacaagcgga tggtacttat gccgttgcac cacgtatctt tacgagttca    960
atagtcaaag atagcttcct gctagggcct aaatttatgc acttattagg tggcggagag  1020
gcaccgttgg aattctctat tggtgaagat ctatttaatt catttaaaat gccgacctct  1080
tggaatttag atgaaaaaac accattcgaa caattccgag ttgccacggc aacacaaaat  1140
acgcaacact tagatgctgt tttccaaaga atgaaaacag aattcccagt atttgaaaaa  1200
tcagaagttg ttgaacgttg gggtgccgtt gtgagtccaa catttgatga attacctatc  1260
atttctgagg tcaaagaata cccaggctta gtgattaaca cggcaacagt gtggggtatg  1320
acagaaggcc cggcagcggg tgaagtgacc gctgatattg tcatgggcaa gaaacctgtt  1380
attgatccaa cgccgtttag tttggatcgt tttaagaagt aa                     1422
```

<210> SEQ ID NO 11
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 11

```
Met Asn Ile Ser Arg Arg Lys Leu Leu Leu Gly Val Gly Ala Ala Gly
1               5                  10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Ile Gly Ala Gly Ile
    50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

Tyr Ala Gln Ile Ile Ser Tyr Gln Ala Ser Pro Glu Ile Phe Pro Leu
                100                 105                 110

His His Tyr Gly Lys Ile Leu Trp Arg Gly Met Asn Glu Lys Ile Gly
            115                 120                 125

Ala Asp Thr Ser Tyr Arg Thr Gln Gly Arg Val Glu Ala Leu Ala Asp
        130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470

<210> SEQ ID NO 12
<211> LENGTH: 1422
<212> TYPE: DNA
<213> ORGANISM: Artificial Sequence
<220> FEATURE:
<223> OTHER INFORMATION: Synthetic DNA

<400> SEQUENCE: 12

```
atgaacattt caaggagaaa gctacttta ggtgttggtg ctgcgggcgt tttagcaggt      60
ggtgcggctt tagttccaat ggttcgccgt gacggcaaat ttgtggaagc taaatcaaga    120
gcatcatttg ttgaaggtac gcaagggct cttcctaaag aagcagatgt agtgattatt    180
ggtgccggta ttcaagggat catgaccgct attaaccttg ctgaacgtgg tatgagtgtc    240
actatcttag aaaagggtca gattgccggt gagcaatcag gccgtgcata cgcacaaatt    300
attagttacc aagcctcgcc agaaatcttc ccattacacc attatgggaa atattatgg    360
cgtggcatga tgagaaaat tggtgcggat accagttatc gtactcaagg tcgtgtagaa    420
gcgctggcag atgaaaaagc attagataaa gctcaagcgt ggatcaaaac agctaaagaa    480
gcggcaggtt ttgatacacc attaaatact cgcatcatta aggtgaaga gctatcaaat    540
cgcttagtcg gtgctcaaac gccatggact gttgctgcat ttgaagaaga ttcaggctct    600
gttgatcctg aaacaggcac acctgcactc gctcgttatg ccaaacaaat cggtgtgaaa    660
atttatacca actgtgcagt aagaggtatt gaaactgcgg gtggtaaaat ctctgatgtg    720
gtgagtgaga aaggggcgat taaaacgtct caagttgtac tcgctggggg tatctggtcg    780
cgtttattta tgggcaatat gggtattgat atcccaacgc tcaatgtata tctatcacaa    840
caacgtgtct caggggttcc tggtgcacca cgtggtaatg tgcatttacc taatggtatt    900
catttccgcg aacaagcgga tggtacttat gccgttgcac cacgtatctt tacgagttca    960
atagtcaaag atagcttcct gctagggcct aaatttatgc acttattagg tggcggagag   1020
ttaccgttgg aattctctat tggtgaagat ctatttaatt catttaaaat gccgacctct   1080
tggaatttag atgaaaaaac accattcgaa caattccgag ttgccacggc aacacaaaat   1140
acgcaacact tagatgctgt tttccaaaga atgaaaacag aattcccagt atttgaaaaa   1200
tcagaagttg ttgaacgttg gggtgccgtt gtgagtccaa catttgatga attacctatc   1260
atttctgagg tcaaagaata cccaggctta gtgattaaca cggcaacagt gtggggtatg   1320
acagaaggcc cggcagcggg tgaagtgacc gctgatattg tcatgggcaa gaaacctgtt   1380
attgatccaa cgccgtttag tttggatcgt tttaagaagt aa                       1422
```

<210> SEQ ID NO 13
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 13

```
Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
            20                  25                  30

Lys Phe Val Glu Ala Lys Ser Arg Ala Ser Phe Val Glu Gly Thr Gln
        35                  40                  45

Gly Ala Leu Pro Lys Glu Ala Asp Val Val Ile Ile Gly Ala Gly Ile
    50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

```
Tyr Ala Gln Ile Ile Ser Tyr Gln Ala Ala Pro Glu Ile Phe Pro Leu
            100                 105                 110

His His Tyr Gly Lys Ile Leu Trp Arg Gly Met Asn Glu Lys Ile Gly
        115                 120                 125

Ala Asp Thr Ser Tyr Arg Thr Gln Gly Arg Val Glu Ala Leu Ala Asp
    130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
    210                 215                 220

Cys Ala Val Arg Gly Ile Glu Thr Ala Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
    290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Leu Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470

<210> SEQ ID NO 14
<211> LENGTH: 1422
<212> TYPE: DNA
<213> ORGANISM: Artificial Sequence
<220> FEATURE:
<223> OTHER INFORMATION: Synthetic DNA
```

<400> SEQUENCE: 14

```
atgaacattt caaggagaaa gctactttta ggtgttggtg ctgcgggcgt tttagcaggt    60
ggtgcggctt tagttccaat ggttcgccgt gacggcaaat tgtgtggaagc taaatcaaga  120
gcatcatttg ttgaaggtac gcaaggggct cttcctaaag aagcagatgt agtgattatt  180
ggtgccggta ttcaagggat catgaccgct attaaccttg ctgaacgtgg tatgagtgtc  240
actatcttag aaaagggtca gattgccggt gagcaatcag gccgtgcata cgcacaaatt  300
attagttacc aagccgcacc agaaatcttc ccattacacc attatgggaa atattatgg   360
cgtggcatga tgagaaaat tggtgcggat accagttatc gtactcaagg tcgtgtagaa   420
gcgctggcag atgaaaaagc attagataaa gctcaagcgt ggatcaaaac agctaaagaa  480
gcggcaggtt ttgatacacc attaaatact cgcatcatta aggtgaaga gctatcaaat   540
cgcttagtcg gtgctcaaac gccatggact gttgctgcat ttgaagaaga ttcaggctct  600
gttgatcctg aaacaggcac acctgcactc gctcgttatg ccaaacaaat cggtgtgaaa  660
atttatacca actgtgcagt aagaggtatt gaaactgcgg gtggtaaaat ctctgatgtg  720
gtgagtgaga aaggggcgat taaaacgtct caagttgtac tcgctggggg tatctggtcg  780
cgtttatta tgggcaatat gggtattgat atcccaacgc tcaatgtata tctatcacaa  840
caacgtgtct caggggttcc tggtgcacca cgtggtaatg tgcatttacc taatggtatt  900
catttccgcg aacaagcgga tggtacttat gccgttgcac cacgtatctt tacgagttca  960
atagtcaaag atagcttcct gctagggcct aaatttatgc acttattagg tggcggagag 1020
ttaccgttgg aattctctat tggtgaagat ctatttaatt catttaaaat gccgacctct 1080
tggaatttag atgaaaaaac accattcgaa caattccgag ttgccacggc aacacaaaat 1140
acgcaacact tagatgctgt tttccaaaga atgaaaacag aattcccagt attttgaaaaa 1200
tcagaagttg ttgaacgttg gggtgccgtt gtgagtccaa catttgatga attacctatc 1260
atttctgagg tcaaagaata cccaggctta gtgattaaca cggcaacagt gtggggtatg 1320
acagaaggcc cggcagcggg tgaagtgacc gctgatattg tcatgggcaa gaaacctgtt 1380
attgatccaa cgccgtttag tttggatcgt tttaagaagt aa                    1422
```

<210> SEQ ID NO 15
<211> LENGTH: 473
<212> TYPE: PRT
<213> ORGANISM: Artificial Sequence
<220> FEATURE:
<223> OTHER INFORMATION: Protein translated from synthetic DNA

<400> SEQUENCE: 15

```
Met Asn Ile Ser Arg Arg Lys Leu Leu Leu Gly Val Gly Ala Ala Gly
1               5                   10                  15

Val Leu Ala Gly Gly Ala Ala Leu Val Pro Met Val Arg Arg Asp Gly
                20                  25                  30

Lys Phe Val Glu Ala Lys Ser Arg Ala Ser Phe Val Glu Gly Thr Gln
            35                  40                  45

Gly Ala Leu Pro Lys Glu Ala Asp Val Val Ile Ile Gly Ala Gly Ile
        50                  55                  60

Gln Gly Ile Met Thr Ala Ile Asn Leu Ala Glu Arg Gly Met Ser Val
65                  70                  75                  80

Thr Ile Leu Glu Lys Gly Gln Ile Ala Gly Glu Gln Ser Gly Arg Ala
                85                  90                  95
```

-continued

```
Tyr Ala Gln Ile Ile Ser Tyr Gln Ala Ala Pro Glu Ile Phe Pro Leu
                100                 105                 110

His His Tyr Gly Lys Ile Leu Trp Arg Gly Met Asn Glu Lys Ile Gly
            115                 120                 125

Ala Asp Thr Ser Tyr Arg Thr Gln Gly Arg Val Glu Ala Leu Ala Asp
        130                 135                 140

Glu Lys Ala Leu Asp Lys Ala Gln Ala Trp Ile Lys Thr Ala Lys Glu
145                 150                 155                 160

Ala Ala Gly Phe Asp Thr Pro Leu Asn Thr Arg Ile Ile Lys Gly Glu
                165                 170                 175

Glu Leu Ser Asn Arg Leu Val Gly Ala Gln Thr Pro Trp Thr Val Ala
            180                 185                 190

Ala Phe Glu Glu Asp Ser Gly Ser Val Asp Pro Glu Thr Gly Thr Pro
        195                 200                 205

Ala Leu Ala Arg Tyr Ala Lys Gln Ile Gly Val Lys Ile Tyr Thr Asn
210                 215                 220

Cys Ala Val Arg Gly Ile Glu Thr Ala Gly Lys Ile Ser Asp Val
225                 230                 235                 240

Val Ser Glu Lys Gly Ala Ile Lys Thr Ser Gln Val Val Leu Ala Gly
                245                 250                 255

Gly Ile Trp Ser Arg Leu Phe Met Gly Asn Met Gly Ile Asp Ile Pro
            260                 265                 270

Thr Leu Asn Val Tyr Leu Ser Gln Gln Arg Val Ser Gly Val Pro Gly
        275                 280                 285

Ala Pro Arg Gly Asn Val His Leu Pro Asn Gly Ile His Phe Arg Glu
        290                 295                 300

Gln Ala Asp Gly Thr Tyr Ala Val Ala Pro Arg Ile Phe Thr Ser Ser
305                 310                 315                 320

Ile Val Lys Asp Ser Phe Leu Leu Gly Pro Lys Phe Met His Leu Leu
                325                 330                 335

Gly Gly Gly Glu Ala Pro Leu Glu Phe Ser Ile Gly Glu Asp Leu Phe
            340                 345                 350

Asn Ser Phe Lys Met Pro Thr Ser Trp Asn Leu Asp Glu Lys Thr Pro
        355                 360                 365

Phe Glu Gln Phe Arg Val Ala Thr Ala Thr Gln Asn Thr Gln His Leu
    370                 375                 380

Asp Ala Val Phe Gln Arg Met Lys Thr Glu Phe Pro Val Phe Glu Lys
385                 390                 395                 400

Ser Glu Val Val Glu Arg Trp Gly Ala Val Ser Pro Thr Phe Asp
                405                 410                 415

Glu Leu Pro Ile Ile Ser Glu Val Lys Glu Tyr Pro Gly Leu Val Ile
            420                 425                 430

Asn Thr Ala Thr Val Trp Gly Met Thr Glu Gly Pro Ala Ala Gly Glu
        435                 440                 445

Val Thr Ala Asp Ile Val Met Gly Lys Lys Pro Val Ile Asp Pro Thr
    450                 455                 460

Pro Phe Ser Leu Asp Arg Phe Lys Lys
465                 470
```

<210> SEQ ID NO 16
<211> LENGTH: 1422
<212> TYPE: DNA
<213> ORGANISM: Artificial Sequence
<220> FEATURE:
<223> OTHER INFORMATION: Synthetic DNA

<400> SEQUENCE: 16

```
atgaacattt caaggagaaa gctactttta ggtgttggtg ctgcgggcgt tttagcaggt      60
ggtgcggctt tagttccaat ggttcgccgt gacggcaaat ttgtggaagc taaatcaaga     120
gcatcatttg ttgaaggtac gcaagggggct cttcctaaag aagcagatgt agtgattatt     180
ggtgccggta ttcaagggat catgaccgct attaaccttg ctgaacgtgg tatgagtgtc     240
actatcttag aaaagggtca gattgccggt gagcaatcag gccgtgcata cgcacaaatt     300
attagttacc aagccgcacc agaaatcttc ccattacacc attatgggaa aatattatgg     360
cgtggcatga atgagaaaat tggtgcggat accagttatc gtactcaagg tcgtgtagaa     420
gcgctggcag atgaaaaagc attagataaa gctcaagcgt ggatcaaaac agctaaagaa     480
gcggcaggtt ttgatacacc attaaatact cgcatcatta aggtgaaga gctatcaaat     540
cgcttagtcg gtgctcaaac gccatggact gttgctgcat ttgaagaaga ttcaggctct     600
gttgatcctg aaacaggcac acctgcactc gctcgttatg ccaaacaaat cggtgtgaaa     660
atttatacca actgtgcagt aagaggtatt gaaactgcgg gtggtaaaat ctctgatgtg     720
gtgagtgaga aaggggcgat taaaacgtct caagttgtac tcgctggggg tatctggtcg     780
cgtttattta tgggcaatat gggtattgat atcccaacgc tcaatgtata tctatcacaa     840
caacgtgtct caggggttcc tggtgcacca cgtggtaatg tgcatttacc taatggtatt     900
catttccgcg aacaagcgga tggtacttat gccgttgcac cacgtatctt tacgagttca     960
atagtcaaag atagcttcct gctagggcct aaatttatgc acttattagg tggcggagag    1020
gcaccgttgg aattctctat tggtgaagat ctatttaatt catttaaaat gccgacctct    1080
tggaattttag atgaaaaaac accattcgaa caattccgag ttgccacggc aacacaaaat    1140
acgcaacact agatgctgt tttccaaaga atgaaaacag aattcccagt attttgaaaaa    1200
tcagaagttg ttgaacgttg gggtgccgtt gtgagtccaa catttgatga attacctatc    1260
atttctgagg tcaaagaata cccaggctta gtgattaaca cggcaacagt gtggggtatg    1320
acagaaggcc cggcagcggg tgaagtgacc gctgatattg tcatgggcaa gaaacctgtt    1380
attgatccaa cgccgtttag tttggatcgt tttaagaagt aa                       1422
```

<210> SEQ ID NO 17
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(14)
<223> OTHER INFORMATION: n is a, c, g, or t

<400> SEQUENCE: 17

```
ggccgtgcat acnnkcaaat tattagt                                          27
```

<210> SEQ ID NO 18
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(15)
<223> OTHER INFORMATION: n is a, c, g, or t

```
<400> SEQUENCE: 18
actaataatt tgmnngtatg cacggcc                                              27

<210> SEQ ID NO 19
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(14)
<223> OTHER INFORMATION: n is a, c, g, or t

<400> SEQUENCE: 19
attagttacc aannktcgcc agaaatc                                              27

<210> SEQ ID NO 20
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(15)
<223> OTHER INFORMATION: n is a, c, g, or t

<400> SEQUENCE: 20
gatttctggc gamnnttggt aactaat                                              27

<210> SEQ ID NO 21
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(14)
<223> OTHER INFORMATION: n is a, c, g, or t

<400> SEQUENCE: 21
agttaccaaa cannkccaga aatcttc                                              27

<210> SEQ ID NO 22
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(15)
<223> OTHER INFORMATION: n is a, c, g, or t

<400> SEQUENCE: 22
gaagatttct ggmnntgttt ggtaact                                              27

<210> SEQ ID NO 23
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (13)..(14)
<223> OTHER INFORMATION: n is a, c, g, or t
```

<400> SEQUENCE: 23
ggtggcggag agnnkccgtt ggaattc                                27

<210> SEQ ID NO 24
<211> LENGTH: 27
<212> TYPE: DNA
<213> ORGANISM: Artificial Sequence
<220> FEATURE:
<223> OTHER INFORMATION: Synthetic DNA
<220> FEATURE:
<221> NAME/KEY: misc_feature
<222> LOCATION: (14)..(15)
<223> OTHER INFORMATION: n is a, c, g, or t

<400> SEQUENCE: 24
gaattccaac ggmnnctctc cgccacc                                27

<210> SEQ ID NO 25
<211> LENGTH: 27
<212> TYPE: DNA
<213> ORGANISM: Artificial Sequence
<220> FEATURE:
<223> OTHER INFORMATION: Synthetic DNA

<400> SEQUENCE: 25
attagttacc aagcctcgcc agaaatc                                27

<210> SEQ ID NO 26
<211> LENGTH: 27
<212> TYPE: DNA
<213> ORGANISM: Artificial Sequence
<220> FEATURE:
<223> OTHER INFORMATION: Synthetic DNA

<400> SEQUENCE: 26
gatttctggc gaggcttggt aactaat                                27

<210> SEQ ID NO 27
<211> LENGTH: 27
<212> TYPE: DNA
<213> ORGANISM: Artificial Sequence
<220> FEATURE:
<223> OTHER INFORMATION: Synthetic DNA

<400> SEQUENCE: 27
agttaccaaa cagcaccaga aatcttc                                27

<210> SEQ ID NO 28
<211> LENGTH: 27
<212> TYPE: DNA
<213> ORGANISM: Artificial Sequence
<220> FEATURE:
<223> OTHER INFORMATION: Synthetic DNA

<400> SEQUENCE: 28
gaagatttct ggtgctgttt ggtaact                                27

<210> SEQ ID NO 29
<211> LENGTH: 27
<212> TYPE: DNA
<213> ORGANISM: Artificial Sequence
<220> FEATURE:
<223> OTHER INFORMATION: Synthetic DNA

<400> SEQUENCE: 29

```
ggtggcggag aggcaccgtt ggaattc                                            27

<210> SEQ ID NO 30
<211> LENGTH: 27
<212> TYPE: DNA
<213> ORGANISM: Artificial Sequence
<220> FEATURE:
<223> OTHER INFORMATION: Synthetic DNA

<400> SEQUENCE: 30
gaattccaac ggtgcctctc cgccacc                                            27

<210> SEQ ID NO 31
<211> LENGTH: 27
<212> TYPE: DNA
<213> ORGANISM: Artificial Sequence
<220> FEATURE:
<223> OTHER INFORMATION: Synthetic DNA

<400> SEQUENCE: 31
agttaccaag ccgcaccaga aatcttc                                            27

<210> SEQ ID NO 32
<211> LENGTH: 27
<212> TYPE: DNA
<213> ORGANISM: Artificial Sequence
<220> FEATURE:
<223> OTHER INFORMATION: Synthetic DNA

<400> SEQUENCE: 32
gaagatttct ggtgcggctt ggtaact                                            27
```